United States Patent
Kawamura et al.

(10) Patent No.: US 10,640,445 B2
(45) Date of Patent: May 5, 2020

(54) METHOD OF PRODUCING LACTIC ACID AND POLYLACTIC ACID

(71) Applicant: Toray Industries, Inc., Tokyo (JP)

(72) Inventors: Kenji Kawamura, Kamakura (JP); Miyuki Horiguchi, Kamakura (JP); Satoshi Sakami, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 27 days.

(21) Appl. No.: 14/916,651

(22) PCT Filed: Sep. 5, 2014

(86) PCT No.: PCT/JP2014/073454
§ 371 (c)(1),
(2) Date: Mar. 4, 2016

(87) PCT Pub. No.: WO2015/034036
PCT Pub. Date: Mar. 12, 2015

(65) Prior Publication Data
US 2016/0207868 A1    Jul. 21, 2016

(30) Foreign Application Priority Data

Sep. 6, 2013 (JP) .................... 2013-184762

(51) Int. Cl.
| | | |
|---|---|---|
| *C07C 51/42* | (2006.01) | |
| *C07C 51/44* | (2006.01) | |
| *C07C 51/47* | (2006.01) | |
| *B01D 61/02* | (2006.01) | |
| *C07C 51/43* | (2006.01) | |
| *C08G 63/06* | (2006.01) | |
| *C12P 7/56* | (2006.01) | |

(52) U.S. Cl.
CPC ............ *C07C 51/44* (2013.01); *B01D 61/027* (2013.01); *C07C 51/43* (2013.01); *C07C 51/47* (2013.01); *C08G 63/06* (2013.01); *C12P 7/56* (2013.01)

(58) Field of Classification Search
CPC .......... C12P 7/56; C07C 59/08; B01D 61/027
See application file for complete search history.

(56) References Cited

U.S. PATENT DOCUMENTS

| | | | |
|---|---|---|---|
| 6,229,046 B1 * | 5/2001 | Eyal .................. | C07C 51/48 562/589 |
| 6,630,603 B1 | 10/2003 | Van Breugel et al. | |
| 2010/0190222 A1 | 7/2010 | Ito et al. | |
| 2011/0263811 A1 | 10/2011 | Sawai et al. | |
| 2014/0051138 A1 | 2/2014 | Na et al. | |

FOREIGN PATENT DOCUMENTS

| | | | |
|---|---|---|---|
| CN | 001161316 | * | 8/2004 |
| CN | 101234960 | * | 8/2008 |
| JP | 2002-540090 A | | 11/2002 |
| JP | 2009-034030 A | | 2/2009 |
| JP | 2009-201506 A | | 9/2009 |
| JP | 2010-189310 A | | 9/2010 |
| JP | 2012-012322 A | | 1/2012 |
| WO | 2009/004922 A | | 1/2009 |
| WO | 2010/074222 A1 | | 7/2010 |
| WO | 2012/147903 A1 | | 11/2012 |

OTHER PUBLICATIONS

Komesu et al "Lactic Acid Purification by Hybrid Short Path Evaporation", Chemical Engineering Transactions, vol. 32, 2013 pp. 2017-2022, published on Jun. 20, 2013.*

* cited by examiner

*Primary Examiner* — Gregory Listvoyb
(74) *Attorney, Agent, or Firm* — DLA Piper LLP (US)

(57) ABSTRACT

A method of producing lactic acid includes filtering a lactic acid-containing aqueous solution through a nanofiltration membrane to recover an aqueous lactic acid solution from the permeate side (Step A); distilling the aqueous lactic acid solution to recover lactic acid from the vapor side (Step B); and crystallizing the lactic acid obtain in Step B, and performing solid-liquid separation to recover a lactic acid crystal(s) (Step C).

7 Claims, 1 Drawing Sheet

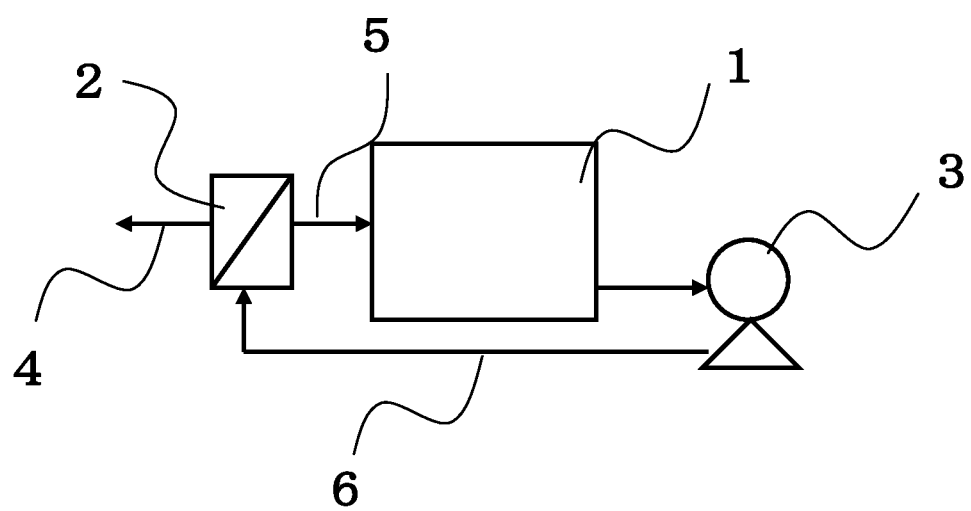

METHOD OF PRODUCING LACTIC ACID AND POLYLACTIC ACID

TECHNICAL FIELD

This disclosure relates to a method of isolating and purifying lactic acid with high purity from a lactic acid-containing aqueous solution, and a method of producing polylactic acid.

BACKGROUND

2-Hydroxypropionic acid, that is, lactic acid, is widely applied not only to uses such as food and pharmaceuticals, but also to industrial uses as a monomer material for plastics, and has been increasingly demanded. Lactic acid is known to be produced by, in addition to chemical synthesis, fermentation by microorganisms, wherein the microorganisms convert substrates containing hydrocarbons such as glucose into lactic acid. Lactic acid is divided into optical isomers, the (L)-isomer and the (D)-isomer based on the conformation of the substituent bound to the carbon at the α-position of carbonyl. By appropriately selecting the microorganism for microbial fermentation, (L)- or (D)-lactic acid can be selectively produced, or lactic acid as a mixture of the (L)-isomer and the (D)-isomer (racemic body) can be produced.

Production of lactic acid by microbial fermentation is generally carried out while a pH appropriate for the microbial fermentation is maintained by addition of an alkaline substance (e.g., calcium hydroxide) to the culture broth. Most of the lactic acid produced as an acidic substance by the microbial fermentation is present as a lactic acid salt (e.g., calcium lactate) in the culture broth due to the addition of the alkaline substance. In general, when lactic acid is used as monomers for a plastic, the lactic acid is preferably lactic acid in the free form obtained by adding an acidic substance (e.g., sulfuric acid) to the culture broth after completion of the fermentation. However, the lactic acid fermentation broth obtained by microbial fermentation contains, other than lactic acid as the product of interest, organic acids and salts thereof, proteins, amino acids, and nonionic compounds such as glycerol, as impurities. When the lactic acid is used as monomers for a plastic, the lactic acid needs to be separated from these impurities.

As a method of removing impurities from a lactic acid-containing aqueous solution and recovering lactic acid, a method based on crystallization of lactic acid is known. In the crystallization, lactic acid is precipitated as crystals to increase the chemical purity as well as the optical purity of the lactic acid, and most of impurities are distributed into the liquid component (mother liquor). As an example of purification of lactic acid by crystallization, Japanese Translated PCT Patent Application Laid-open No. 2002-540090 discloses a method in which an aqueous lactic acid solution is distilled, and crystallization is then performed to recover high-quality lactic acid. WO 2009/004922 discloses a method in which a lactic acid-containing solution derived from microbial fermentation is passed through a nanofiltration membrane, and crystallization of lactic acid is then performed to increase the yield.

We found a problem in the conventional methods that, when lactic acid crystals are obtained by crystallization from a lactic acid-containing solution and the obtained lactic acid crystals are recovered by solid-liquid separation, the recovered lactic acid crystals cannot be easily separated from the liquid so that the purity of the lactic acid is low.

It could therefore be helpful to provide, when lactic acid crystals are obtained by crystallization from a lactic acid-containing solution and the obtained lactic acid crystals are recovered by solid-liquid separation, a method of obtaining lactic acid crystals exhibiting excellent separation from the liquid (solid-liquid separation performance).

SUMMARY

We discovered that lactic acid crystals having not only high purity, but also excellent solid-liquid separation performance can be obtained by carrying out a step of passing a lactic acid-containing aqueous solution through a nanofiltration membrane to recover an aqueous lactic acid solution from the permeate side, and a step of distilling the aqueous lactic acid solution to recover lactic acid from the vapor side, as steps preceding crystallization of the lactic acid. We also discovered that polylactic acid obtained using as a material the lactic acid obtained by our methods has excellent physical properties.

We thus provide (1) to (4) described below:
(1) A method of producing lactic acid, the method comprising the steps of:
  filtering a lactic acid-containing aqueous solution through a nanofiltration membrane to recover an aqueous lactic acid solution from the permeate side (Step A);
  distilling the aqueous lactic acid solution to recover lactic acid from the vapor side (Step B); and
  crystallizing the lactic acid obtained in Step B, and performing solid-liquid separation to recover a lactic acid crystal(s) (Step C).
(2) The method of producing lactic acid according to (1), wherein the lactic acid-containing aqueous solution is derived from microbial fermentation.
(3) A method of producing polylactic acid, the method comprising the steps of:
  producing lactic acid by the method of producing lactic acid according to (1) or (2); and
  producing polylactic acid using the lactic acid as a material (Step D).
(4) The method of producing polylactic acid according to (3), wherein the Step (D) is a step of direct dehydration polycondensation of the lactic acid.

Lactic acid crystals having high purity and excellent solid-liquid separation performance can be produced.

BRIEF DESCRIPTION OF THE DRAWING

FIG. 1 is a schematic diagram showing an example of a membrane separation device used in our methods.

DESCRIPTION OF SYMBOLS

1. Supply tank
2. Nanofiltration membrane element
3. High-pressure pump
4. Flow of permeate from nanofiltration membrane
5. Flow of non-permeate of nanofiltration membrane
6. Flow of supply liquid for nanofiltration membrane

DETAILED DESCRIPTION

Our method of producing lactic acid comprises the steps of: filtering a lactic acid-containing aqueous solution through a nanofiltration membrane to recover lactic acid from the permeate side (Step A); distilling the aqueous lactic acid solution after Step A to recover lactic acid from the vapor side (Step B); and crystallizing the lactic acid obtained in Step B, and performing solid-liquid separation to recover a lactic acid crystal(s) (Step C). The method is described below in more detail.

The origin of the lactic acid-containing aqueous solution is not limited as long as the solution contains lactic acid in the free form (which may be hereinafter referred to as free lactic acid). The solution may be an aqueous solution of lactic acid obtained by organic synthesis, or may be derived from microbial fermentation, that is, may be a lactic acid fermentation culture broth per se obtained by microbial fermentation or a lactic acid fermentation culture broth processed through a plurality of separation/purification steps. The lactic acid-containing aqueous solution is preferably derived from microbial fermentation. When the lactic acid-containing aqueous solution is derived from microbial fermentation, an alkaline substance is generally added to adjust the pH during the culture. Thus, it is known that the lactic acid in the lactic acid fermentation culture broth may be present as a lactic acid salt. In such cases, as a pretreatment before subjecting the lactic acid-containing aqueous solution to Step A, the lactic acid salt in the lactic acid fermentation culture broth may be converted to free lactic acid by a known method.

Specific examples of the lactic acid salt include lithium lactate, sodium lactate, potassium lactate, calcium lactate, magnesium lactate, aluminum lactate, and ammonium lactate, and mixtures of two or more thereof. As a method of obtaining free lactic acid from such a lactic acid salt, a method by adding an acidic substance can be employed. The acidic substance is not limited, and sulfuric acid, hydrochloric acid, carbonic acid, phosphoric acid, nitric acid, or the like may be used. Sulfuric acid is preferably used to form the later-described insoluble salt. The aqueous lactic acid salt solution is preferably converted to an aqueous solution containing free lactic acid by addition of the acidic substance, while the cationic component of the lactic acid salt is removed as an insoluble salt. By adding the acidic substance to the aqueous lactic acid salt solution to cause precipitation of the cationic component in the solution as an insoluble salt and then performing solid-liquid separation by filtration or the like, an aqueous solution of free lactic acid from which cationic ions derived from the lactic acid salt have been removed can be obtained. The method of solid-liquid separation of the insoluble salt is not limited, and a method known to those skilled in the art such as filtration through qualitative filter paper or centrifugation may be applied. When a large amount of free lactic acid is contained in the fermentation broth, for example, when a lactic acid fermentation culture liquid obtained by lactic acid fermentation at a low pH (for example, with a pKa of lactic acid of not more than 3.86) is used, the fermentation culture broth may be subjected as it is to Step A.

In our method the lactic acid-containing aqueous solution is subjected to a step of filtration through a nanofiltration membrane to recover an aqueous lactic acid solution from the permeate side of the membrane (Step A). The solution obtained in the permeate side after the filtration of a lactic acid-containing aqueous solution through a nanofiltration membrane is referred to as aqueous lactic acid solution to distinguish this solution from the lactic acid-containing aqueous solution.

The nanofiltration membrane is also called nanofiltration membrane or NF membrane, and generally defined as a "membrane that allows permeation of monovalent ions, but blocks divalent ions." The membrane has fine voids having sizes of about several nanometers, and mainly used to block fine particles, molecules, ions, salts, and/or the like in water.

Examples of the material of the nanofiltration membrane include polymer materials such as piperazine polyamide, polyamide, cellulose acetate, polyvinyl alcohol, polyimide, and polyester; and inorganic materials such as ceramics. A nanofiltration membrane is generally used as a spiral-wound membrane element or a flat membrane or hollow fiber membrane. The nanofiltration membrane is preferably a spiral-wound membrane element.

Specific examples of the nanofiltration membrane element preferably include "GEsepa," which is a cellulose acetate nanofiltration membrane manufactured by GE Osmonics; NF99 and NF99HF, which are nanofiltration membranes having a functional layer composed of a polyamide, manufactured by Alfa-Laval; NF-45, NF-90, NF-200, and NF-400, which are nanofiltration membranes having a functional layer composed of a cross-linked piperazine polyamide, manufactured by Filmtec Corporation; and SU-210, SU-220, SU-600, and SU-610, which are nanofiltration membrane elements manufactured by Toray Industries, Inc., containing UTC60 manufactured by the same manufacturer. Among these, the nanofiltration membrane element is more preferably NF99 or NF99HF, which are nanofiltration membranes having a functional layer composed of a polyamide, manufactured by Alfa-Laval; NF-45, NF-90, NF-200, or NF-400, which are nanofiltration membranes having a functional layer composed of a cross-linked piperazine polyamide, manufactured by Filmtec Corporation; or SU-210, SU-220, SU-600, or SU-610, which are nanofiltration membrane modules manufactured by Toray Industries, Inc., containing UTC60 manufactured by the same manufacturer. The nanofiltration membrane element is still more preferably SU-210, SU-220, SU-600, or SU-610, which are nanofiltration membrane elements manufactured by Toray Industries, Inc., containing UTC60 manufactured by the same manufacturer, whose major component is a cross-linked piperazine polyamide.

Filtration through a nanofiltration membrane may be carried out under pressure and the filtration pressure is preferably 0.1 MPa to 8 MPa. When the filtration pressure is less than 0.1 MPa, the membrane permeation rate may be low, while when the filtration pressure is more than 8 MPa, the membrane may be damaged. When the membrane is used at a filtration pressure of 0.5 MPa to 7 MPa, the membrane permeation flux is high so that the lactic acid-containing aqueous solution can be efficiently allowed to permeate, and the possibility of damaging the membrane is small, which is more preferred. The membrane is especially preferably used at a filtration pressure of 1 MPa to 6 MPa.

The concentration of the lactic acid to be filtered through the nanofiltration membrane is not limited. When the concentration is high, the concentration of lactic acid contained in the permeate is also high so that the energy to concentrate the solution can be reduced and the cost can therefore be favorably reduced. The lactic acid remaining in the feed side of the nanofiltration membrane may be recycled in Step A. By this, the total yield of lactic acid can be improved.

In our method the Step A described above is followed by a step of distilling the aqueous lactic acid solution to recover lactic acid from the vapor side (Step B).

The lactic acid concentration in the aqueous lactic acid solution to be subjected to the distillation step is not limited. When the lactic acid concentration in the solution is too low, a large distillation equipment is necessary, while when the concentration is too high, oligomerization may occur, leading to a low yield. Thus, the distillation can be preferably carried out when the concentration of lactic acid is 40 to 95 wt %, more preferably 60 to 90 wt%. The distillation step is carried out under a reduced pressure of not less than 1 Pa and not more than atmospheric pressure (normal pressure, about 101 kPa). When the step is carried out under a reduced pressure of 10 Pa to 30 kPa, the distillation temperature can be lowered, which is more preferred. The distillation temperature when the step is carried out under reduced pressure is 20° C. to 200° C., but, when the distillation is carried out at a temperature of not less than 180° C., racemization of lactic acid may be caused by the influence of impurities. Therefore, the distillation of lactic acid can be preferably carried out at a temperature of 50° C. to 180° C., more preferably 60° C. to 150° C.

Since lactic acid is likely to undergo oligomerization under dehydration conditions (by heating and/or under reduced pressure) because of its structure, the residence time is preferably as short as possible. Accordingly, a film evaporator such as a falling-film evaporator or wiped film evaporator is preferably used as the evaporator since it enables achievement of a reduced distillation time and can therefore increase the recovery of lactic acid. Continuous distillation, that is, continuous supply of the lactic acid-containing aqueous solution and continuous recovery of lactic acid from the vapor side, may be carried out using the evaporator. The lactic acid vaporized by the evaporator is recovered by cooling in a condenser. Since the vapor phase contains not only lactic acid, but also water and low boiling components, a plurality of condensers may be used such that, for example, lactic acid and, in some cases, an arbitrary proportion of water are condensed in a first-stage condenser, and the remaining water and low boiling components are condensed in the second-stage condenser.

When the concentration of the aqueous lactic acid solution to be subjected to Step B is low, the lactic acid is preferably concentrated prior to Step B. The method of concentrating the lactic acid-containing aqueous solution may be a common method known to those skilled in the art, and examples of the method include methods using a reverse osmosis membrane, concentration under heat using an evaporator, and distillation. Two or more of these methods may be used in combination. A method using a reverse osmosis membrane is preferably applied from the viewpoint of reduction of the energy for the concentration.

A reverse osmosis membrane is also called an RO membrane. Since reverse osmosis membranes have higher blocking rates of monovalent ions relative to nanofiltration membranes, a large amount of reverse osmosis membranes are used for seawater desalination and in the field of electronic industry, in which ultrapure water for washing semiconductors is required.

In the methods using a reverse osmosis membrane, the lactic acid-containing aqueous solution is filtered through a reverse osmosis membrane to allow permeation of water into the permeate side of the membrane, while retaining lactic acid in the feed side of the membrane, thereby concentrating lactic acid. Preferred examples of the reverse osmosis membrane include composite membranes having a cellulose acetate polymer as a functional layer (which may be hereinafter referred to as cellulose acetate reverse osmosis membranes) and composite membranes having a polyamide functional layer (which may be hereinafter referred to as polyamide reverse osmosis membranes). Examples of the cellulose acetate polymer include organic acid esters of cellulose such as cellulose acetate, cellulose diacetate, cellulose triacetate, cellulose propionate, and cellulose butyrate. These may be used individually, or two or more of these may be used as a mixture or a mixed ester. Examples of the polyamide include linear polymers and cross-linked polymers constituted by aliphatic and/or aromatic diamine monomers. Examples of the form of the membrane that may be used as appropriate include flat membranes, spiral-wound membranes, and hollow fiber membranes.

Specific examples of the reverse osmosis membrane include polyamide reverse osmosis membrane modules manufactured by Toray Industries, Inc. such as SU-710, SU-720, SU-720F, SU-710L, SU-720L, SU-720LF, SU-720R, SU-710P, SU-720P, SU-810, SU-820, SU-820L, SU-820FA, TM800, TM800C, TM800A, TM800H, TM800E, and TM800L; cellulose acetate reverse osmosis membranes manufactured by the same manufacturer, SC-L100R, SC-L200R, SC-1100, SC-1200, SC-2100, SC-2200, SC-3100, SC-3200, SC-8100, and SC-8200; NTR-759HR, NTR-729HF, NTR-70SWC, ES10-D, ES20-D, ES20-U, ES15-D, ES15-U, and LF10-D, manufactured by Nitto Denko Corporation; RO98pHt, R099, HR98PP, and CE4040C-30D, manufactured by Alfa-Laval; "GE Sepa," manufactured by GE; and BW30-4040, TW30-4040, XLE-4040, LP-4040, LE-4040, SW30-4040, and SW3OHRLE-4040, manufactured by FilmTec Corporation.

The concentration with a reverse osmosis membrane is carried out under pressure. The filtration pressure is preferably 1 MPa to 8 MPa since, when the filtration pressure is less than 1 MPa, the membrane permeation rate may be low, while when the filtration pressure is more than 8 MPa, the membrane may be damaged. When the filtration pressure is 1 MPa to 7 MPa, the membrane permeation flux is high so that the lactic acid-containing aqueous solution can be efficiently concentrated. The filtration pressure is most preferably 2 MPa to 6 MPa in view of reducing the possibility of damaging the membrane. In a lactic acid-containing aqueous solution at a low concentration, a method using a reverse osmosis membrane is especially preferred in view of the cost.

Subsequently, the lactic acid recovered in Step B is subjected to a step (Step C) of crystallization followed by recovery of a lactic acid crystal(s) by solid-liquid separation. By subjecting the lactic acid processed through Step A and Step B, to Step C, lactic acid crystals having a better solid-liquid separation performance than that of lactic acid crystals obtained by conventional lactic acid crystallization can be obtained.

The method of crystallization of lactic acid in Step C is not limited, and may be carried out by a method ordinarily used. Examples of the method include a method in which the lactic acid-containing aqueous solution is cooled to make lactic acid supersaturated (cooling crystallization), a method in which the solvent (water) is evaporated to make lactic acid supersaturated (evaporative crystallization), and a method in which the solvent (water) is evaporated while the lactic acid solution is cooled, thereby concentrating the solution to make lactic acid supersaturated (insulated crystallization). Among the crystallization methods described above, insulated crystallization may be preferably applied since the input of energy to the cooling can be reduced. Further, in the crystallization, continuous crystallization, that is, continuous supply of the lactic acid-containing aqueous solution and continuous extraction of the lactic acid slurry, may be carried out. In the crystallization, a seed crystal(s) may be added.

Known solid-liquid separation methods may be applied to the solid-liquid separation of the lactic acid crystals and the remaining liquid (mother liquor) in Step C. More specifically, the lactic acid crystals can be recovered by, for example, decantation, centrifugation, or suction filtration using qualitative filter paper. The mother liquor after the recovery of the crystals can be recycled into the fermentation culture liquid, or in a lactic acid production process such as Steps A to C. By this, the total recovery of lactic acid can be increased.

The lactic acid crystals obtained in Step C are characterized in that they have a better solid-liquid separation performance than lactic acid crystals obtained by conventional methods. The solid-liquid separation performance is evaluated using as an index the water content of the lactic acid crystals obtained. The water content of the lactic acid crystals reflects the amount of the mother liquor remaining in the crystals. A high water content indicates the presence of impurities derived from the mother liquor, which results in a low purity of the lactic acid crystals obtained.

The lactic acid crystals obtained in Step C are highly pure and applicable to uses in which high purity is required such as uses as a material of polylactic acid. The mother liquor attached to the crystals may be washed with a washing liquid to obtain crystals having higher purity. From the viewpoint of prevention of dissolution of the produced lactic acid crystals, which leads to a low crystal recovery, the washing liquid is preferably a poor solvent which does not dissolve lactic acid. Such a poor solvent is preferably an aqueous lactic acid solution having a lactic acid concentration of about 80 to 100 wt %. More preferably, a part of the lactic acid crystals are dissolved in water to prepare an aqueous solution having the above-described concentration, and the prepared solution is used as the washing liquid. Since the lactic acid crystals obtained in Step C as described above contain only a small amount of the remaining mother liquor, the amount of the washing liquid can be small. The washing liquid is preferably separated from the washed crystals by the solid-liquid separation method described above, and recycled in the lactic acid production process similarly to the mother liquor in Step C.

We also provide a method of producing polylactic acid, which method comprises a step (Step D) of producing polylactic acid using as a material the lactic acid obtained by the lactic acid production process described above.

Examples of the polylactic acid include homopolymers of L-lactic acid units or D-lactic acid units; polylactic acid block copolymers containing a segment composed of poly-L-lactic acid units and a segment composed of poly-D-lactic acid units; and copolymers with monomers other than lactic acid. When the polylactic acid is a copolymer, examples of the monomer units other than lactic acid include glycol compounds such as ethylene glycol, propylene glycol, butanediol, heptanediol, hexanediol, octanediol, nonanediol, decanediol, 1,4-cyclohexanedimethanol, neopentyl glycol, glycerin, pentaerythritol, bisphenol A, polyethylene glycol, polypropylene glycol, and polytetramethylene glycol; dicarboxylic acids such as oxalic acid, adipic acid, sebacic acid, azelaic acid, dodecanedioic acid, malonic acid, glutaric acid, cyclohexanedicarboxylic acid, terephthalic acid, isophthalic acid, phthalic acid, naphthalenedicarboxylic acid, bis(p-carboxyphenyl)methane, anthracenedicarboxylic acid, diphenyl ether dicarboxylic acid, sodium sulfoisophthalic acid, and tetrabutyl phosphonium isophthalic acid; hydroxycarboxylic acids such as glycolic acid, hydroxypropionic acid, hydroxybutyric acid, hydroxyvaleric acid, hydroxycaproic acid, and hydroxybenzoic acid; and lactones such as caprolactone, valerolactone, propiolactone, undecalactone, and 1,5-oxepan-2-one. The amount of the above-described other copolymerization components to be copolymerized is preferably 0 to 30 mol %, more preferably 0 to 10 mol %, with respect to the total monomer components.

As Step D, a common method of producing polylactic acid may be used. More specifically, known examples of the method include the two-step lactide method, in which lactide, which is a cyclic dimer, is first produced using lactic acid as a material, and ring-opening polymerization is then performed; and the single-step direct polymerization method, in which the material is subjected to direct dehydration polycondensation in a solvent. Either production method may be used. When the direct polymerization method is employed, the lactic acid as a material needs to be highly pure. The lactic acid is sufficiently applicable to the direct polymerization method. The solvent to be used for the direct polymerization method is not limited as long as the solvent does not adversely affect the polymerization, and may be water or an organic solvent. Examples of the organic solvent include aromatic hydrocarbons. Examples of the aromatic hydrocarbons include toluene, xylene, naphthalene, chlorobenzene, and diphenyl ether.

When the polylactic acid is produced by the direct polymerization method, the polymerization can be promoted by removal of water produced by the condensation reaction to the outside of the system. The method of removal to the outside of the system is preferably polymerization under reduced pressure. More specifically, the pressure is preferably not more than 7 kPa, more preferably not more than 1.5 kPa.

The polymerization time can be shortened by using a catalyst for the polymerization reaction. Examples of the catalyst include metals such as tin, zinc, lead, titanium, bismuth, zirconium, germanium, antimony, and aluminum, and derivatives thereof. The derivatives are preferably metal alkoxides, carboxylates, carbonates, oxides, and halides. Specific examples the derivatives include tin chloride, tin octylate, zinc chloride, lead oxide, lead carbonate, titanium chloride, alkoxytitanium, germanium oxide, and zirconium oxide. Among these, tin compounds are preferred, and tin acetate and tin octylate are more preferred.

EXAMPLES

Our methods are described below in more detail by way of Examples, but this disclosure is not restricted to the Examples below.

In the Examples, the lactic acid concentration and physical properties of lactic acid crystals were determined by the following measurement methods.

A. Lactic Acid Concentration

The lactic acid concentration in each step was measured by high-performance liquid chromatography (manufactured by Shimadzu Corporation) under the following conditions:
  Column: Shim-Pack SPR-H (manufactured by Shimadzu Corporation)
  Mobile phase: 5 mMp-toluenesulfonic acid (flow rate: 0.8 mL/min.)
  Reaction solution: 5 mM p-toluenesulfonic acid, 20 mM Bis-Tris, 0.1 mM EDTA•2Na (flow rate: 0.8 mL/min.)
  Detection method: electric conductivity
  Temperature: 45° C.

B. Crystallization Yield

The crystallization yield was calculated according to Equation 1 based on the amount of lactic acid in the liquid supplied in the crystallization step and the amount of lactic acid in the crystals obtained in the crystallization step:

Crystallization yield=100×(amount of lactic acid in crystals)/(amount of lactic acid in supplied liquid in crystallization step)     (1).

C. Water Content of Lactic Acid Crystals

The water content of the lactic acid crystals was measured by subjecting 0.1 g of the crystals to measurement using a Karl-Fischer moisture meter AQ-2200 (manufactured by Hiranuma Sangyo Co., Ltd.). The measurement was carried out three times in the same manner for each sample of crystals, and the average of the measured values was defined as the water content (wt %).

D. Degree of Coloration (APHA) of Lactic Acid Crystals

Pure water was added to the lactic acid crystals to provide 90 wt % aqueous lactic acid solution, and the APHA unit color number was analyzed using a colorimeter (manufactured by Nippon Denshoku Industries Co., Ltd.).

Reference Example 1 Production of Lactic Acid by Batch Fermentation

Lactic acid fermentation using a microorganism was carried out according to Example 4 (pH 4) of WO2012/147903. The obtained D-lactic acid fermentation broth (D-lactic acid concentration, 40 g/L) was used in the following Examples after removal of the cells by filtration through a microfiltration membrane ("Microza," manufactured by Asahi Kasei Corporation).

Example 1 Production Example of Lactic Acid Using Lactic Acid Fermentation Broth as Material Obtaining Free Lactic Acid by Addition of Acidic Substance Concentrated sulfuric acid (manufactured by Wako Pure Chemical Industries, Ltd.) was added dropwise to 20 L of the lactic acid fermentation liquid obtained in Reference Example 1 with stirring to a pH of 2.5. The precipitated calcium sulfate was removed by filtration using Qualitative Filter Paper No. 2 (manufactured by Advantec), and the filtrate was collected as a lactic acid-containing aqueous solution.

Filtration through Nanofiltration Membrane

The lactic acid-containing aqueous solution was purified using the membrane separation device shown in FIG. 1. As a nanofiltration membrane 2, a spiral-wound membrane element "SU-610" (manufactured by Toray Industries, Inc.) was used. To a supply tank 1, 20 L of the lactic acid fermentation broth was injected, and the device was operated at a supply liquid pressure of 2 MPa at a supply liquid temperature of 25° C. By filtration through the nanofiltration membrane, a membrane permeate 4 was collected as an aqueous lactic acid solution.

Distillation of Aqueous Lactic Acid Solution

Using a rotary evaporator (manufactured by Tokyo Rikakikai Co., Ltd.), 6 L of the aqueous lactic acid solution was concentrated by evaporation of water under reduced pressure (50 hPa), to obtain 40 wt % aqueous lactic acid solution. Subsequently, 500 g of the concentrated aqueous lactic acid solution was continuously supplied to the evaporator at a rate of 56.25 g/h, while distillation was performed under a reduced pressure of 600 Pa at 150° C. The first-stage condenser was operated at 45° C., and the second-stage condenser was operated at 2° C. From the first-stage condenser, 196 g of condensed 92 wt % aqueous lactic acid solution was obtained.

Crystallization of Lactic Acid after Distillation

To 120 g of the 92 wt % aqueous lactic acid solution recovered by the distillation, 0.6 g of seed crystals were added, and the resulting mixture was left to stand at 25° C. for 2 hours, thereby allowing crystallization of lactic acid. The resulting slurry containing lactic acid crystals was subjected to suction filtration using Qualitative Filter Paper No. 4 (60-mm diameter, manufactured by Kiriyama Glass Co.) for 15 minutes to perform solid-liquid separation. The crystals were then subjected to centrifugal filtration using "VIVASPIN" 20 (0.2 µm, manufactured by Sartorius) at 13,000 rpm at 25° C. for 20 minutes to obtain lactic acid crystals. The results of evaluation of the crystallization yield, the water content of the crystals, and the degree of coloration of the crystals are shown in Table 1.

Comparative Example 1 Production Example of Lactic Acid without Filtration through Nanofiltration Membrane Obtaining Free Lactic Acid by Addition of Acidic Substance By the same procedure as in Example 1, sulfuric acid was added to 6 L of the lactic acid fermentation broth obtained in Reference Example 1, and the filtrate containing free lactic acid was collected as a lactic acid-containing aqueous solution.

Distillation of Lactic Acid-containing Aqueous Solution

Using a rotary evaporator (manufactured by Tokyo Rikakikai Co., Ltd.), 6 L of the lactic acid-containing aqueous solution was concentrated by evaporation of water under reduced pressure (50 hPa), to obtain 40 wt % lactic acid-containing aqueous solution. Subsequently, 500 g of the concentrated lactic acid-containing aqueous solution was continuously supplied at a rate of 56.25 g/h, while distillation was performed under a reduced pressure of 600 Pa at 150° C. The first-stage condenser was operated at 45° C., and the second-stage condenser was operated at 2° C. From the first-stage condenser, 146 g of condensed 92 wt % aqueous lactic acid solution was obtained.

Crystallization of Lactic Acid after Distillation

To 120 g of the 92 wt % aqueous lactic acid solution recovered by the distillation, 0.6 g of seed crystals were added, and the resulting mixture was left to stand at 25° C. for 2 hours, thereby allowing crystallization of lactic acid. The resulting slurry containing lactic acid crystals was subjected to suction filtration using Qualitative Filter Paper No. 4 (60-mm diameter, manufactured by Kiriyama Glass Co.) for 15 minutes to perform solid-liquid separation. The crystals were then further subjected to centrifugal filtration using "VIVASPIN" 20 (0.2 µm, manufactured by Sartorius) at 13,000 rpm at 25° C. for 20 minutes to obtain lactic acid crystals. The results of evaluation of the crystallization yield, the water content of the crystals, and the degree of coloration of the crystals are shown in Table 1.

Comparative Example 2 Production Example of Lactic Acid without Distillation

Obtaining Free Lactic Acid by Addition of Acidic Substance

By the same procedure as in Example 1, sulfuric acid was added to 20 L of the lactic acid fermentation broth obtained in Reference Example 1, and the filtrate containing free lactic acid was collected as a lactic acid-containing aqueous solution.

Filtration through Nanofiltration Membrane

The fermentation liquid described above was purified using the membrane separation device shown in FIG. 1. As a nanofiltration membrane 2, a spiral-wound membrane element "SU-610" (manufactured by Toray Industries, Inc.) was used. To a supply tank 1, 20 L of the lactic acid fermentation liquid was injected, and the device was operated at a supply liquid pressure of 2 MPa at a supply liquid temperature of 25° C. By filtration through the nanofiltration membrane, a membrane permeate 4 was collected as an aqueous lactic acid solution.

Crystallization of Nanofiltration Membrane Permeate

Using a rotary evaporator (manufactured by Tokyo Rikakikai Co., Ltd.), 4 L of the aqueous lactic acid solution was concentrated by evaporation of water under reduced pressure (50 hPa), to obtain 92 wt % aqueous lactic acid solution. Subsequently, to 120 g of the 92 wt% aqueous lactic acid solution, 0.6 g of seed crystals were added, and the resulting mixture was left to stand at 25° C. for 2 hours, thereby allowing crystallization of lactic acid. The resulting slurry containing lactic acid crystals was subjected to suction filtration using Qualitative Filter Paper No. 4 (60-mm diameter, manufactured by Kiriyama Glass Co.) for 15 minutes to perform solid-liquid separation. The crystals were then further subjected to centrifugal filtration using "VIVASPIN" 20 (0.2 manufactured by Sartorius) at 13,000 rpm at 25° C. for 20 minutes to obtain lactic acid crystals. The results of evaluation of the crystallization yield, the water content of the crystals, and the degree of coloration of the crystals are shown in Table 1.

polylactic acid was analyzed for its weight average molecular weight, melting point, thermal weight loss rate, and degree of coloration.

Analysis of Weight Average Molecular Weight of Polylactic Acid

The weight average molecular weight (Mw) of the polylactic acid produced by the polymerization is a value calculated in terms of the weight average molecular weight of a standard polymethyl methacrylate measured by gel permeation chromatography (GPC). The GPC measurement was carried out using HLC8320GPC (manufactured by Tosoh Corporation) as a GPC system, and two TSK-GEL SuperHM-M columns (manufactured by Tosoh Corporation) connected in series. The detection was carried out using a differential refractometer. The measurement was carried out under the following conditions: flow rate, 0.35 mL/min.; solvent, hexafluoroisopropanol; injection of 0.02 mL of a solution with a sample concentration of 1 mg/mL.

Analysis of Melting Point of Polylactic Acid

The melting point of the polylactic acid obtained by the polymerization was measured using a differential scanning calorimeter DSC7020 (manufactured by SII NanoTechnology Inc.)

TABLE 1

| | Purification steps | | Crystallization yield (%) | Water content (wt %) | Degree of coloration (APHA) |
| | Nanofiltration membrane | Distillation | Crystallization | | | |
| --- | --- | --- | --- | --- | --- | --- |
| Example 1 | Yes | Yes | Yes | 32.3 | 2.5 | 2 |
| Comparative Example 1 | No | Yes | Yes | 30.9 | 3.3 | 4 |
| Comparative Example 2 | Yes | No | Yes | 29.8 | 4.6 | 18 |

As shown in Table 1, the water content in lactic acid crystals was remarkably low in Example 1 since the filtration through the nanofiltration membrane and the distillation were carried out before the crystallization step.

Example 2 Polymerization Test of Lactic Acid, and Evaluation of Physical Properties of Polylactic Acid The lactic acid crystals obtained in Example 1 were subjected to direct dehydration polycondensation, and physical properties of the resulting polylactic acid were analyzed. In a reaction vessel equipped with a stirrer, 30 g of 90 wt % aqueous lactic acid solution prepared by adding water to the lactic acid crystals obtained in Example 1 was heated at 800 Pa at 160° C. for 3.5 hours, to obtain oligomers. Subsequently, 0.024 g of tin (II) acetate (manufactured by Kanto Chemical Co., Ltd.) and 0.066 g of methanesulfonic acid (manufactured by Wako Pure Chemical Industries, Ltd.) were added to the oligomers, and the resulting mixture was heated at 500 Pa at 180° C. for 7 hours, to obtain a prepolymer. The prepolymer was then crystallized by heating in an oven at 120° C. for 2 hours. The obtained prepolymer was pulverized using a hammer mill, and passed through a sieve, to obtain a powder having an average particle size of 0.1 mm. In the solid phase polymerization step, the prepolymer was fed into an oven to which an oil rotary pump was connected, and vacuum heat treatment was carried out. The pressure was set to 50 Pa, and the heating temperature was set to: 140° C. for 10 hours, 150° C. for 10 hours, and 160° C. for 20 hours. The obtained The measurement was carried out with 10 mg of the sample under nitrogen atmosphere at a heating rate of 20° C./minute.

Analysis of Thermal Weight Loss Rate of Polylactic Acid

The thermal weight loss rate of the polylactic acid obtained by the polymerization was measured using a thermo gravimetry differential thermal analyzer TG/DTA7200 (manufactured by SII NanoTechnology Inc.). The measurement was carried out with 10 mg of the sample under nitrogen atmosphere at a constant temperature of 200° C. for a heating time of 20 minutes. The polylactic acid obtained by the direct polymerization of lactic acid had a melting point of 167.3° C. and a thermal weight loss rate of 4.6%.

Analysis of Degree of Coloration of Polylactic Acid

In 37 g of chloroform, 0.4 g of the polylactic acid obtained by the polymerization was completely dissolved, and the degree of coloration was analyzed using a colorimeter (manufactured by Nippon Denshoku Industries Co., Ltd.) in terms of the APHA unit color number.

The results of the analysis of the physical properties of the polylactic acid are shown in Table 2.

Comparative Examples 3 and 4 Polymerization Test of Lactic Acid, and Evaluation of Polylactic Acid Produced by Polymerization By the same procedure as in Example 2 except that the lactic acid obtained in Comparative Example 1 or Comparative Example 2 was used, polylactic acids were produced by polymerization, and their physical properties were analyzed. The results are shown in Table 2.

TABLE 2

|  | Weight average molecular weight (Mw) | Melting point (° C.) | Weight loss rate (%) | Degree of Coloration (APHA) |
|---|---|---|---|---|
| Example 2 | 214000 | 167.5 | 5.1 | 4 |
| Comparative Example 3 | 181000 | 165.1 | 6.1 | 8 |
| Comparative Example 4 | 173000 | 163.4 | 6.5 | 17 |

As can be seen in Table 2, the polylactic acid obtained in Example 2 showed better results in all examined physical properties compared to the polylactic acids obtained in Comparative Example 2 and Comparative Example 3.

INDUSTRIAL APPLICABILITY

The lactic acid obtained by our methods can be favorably used not only for food and pharmaceuticals, but also as a monomer material for polylactic acid, which is a plastic. The polylactic acid can be used as a plastic for industrial uses.

The invention claimed is:

1. A method of producing lactic acid crystal(s) comprising:
   filtering a lactic acid-containing aqueous solution through a nanofiltration membrane to recover an aqueous lactic acid solution from the permeate side (Step A);
   distilling said aqueous lactic acid solution to recover lactic acid from the vapor side (Step B), and performing a first stage condensing step to obtain distilled lactic acid from a first condenser vapor side and a second stage condensing step to remove water and a low boiling component(s) from a second condenser vapor side; and
   crystallizing said lactic acid obtained only in the first stage condensing step from Step B, and performing solid-liquid separation to recover a lactic acid crystal(s) (Step C).

2. The method according to claim 1, wherein said lactic acid-containing aqueous solution is derived by microbial fermentation.

3. A method of producing polylactic acid comprising:
   producing lactic acid crystal(s) by the method according to claim 1; and
   producing polylactic acid using said lactic acid crystal(s) as a material (Step D).

4. The method according to claim 3, wherein Step (D) is a step of direct dehydration polycondensation of lactic acid using said lactic acid crystal(s) as a material.

5. A method of producing polylactic acid comprising:
   producing lactic acid crystal(s) by the method according to claim 2; and
   producing polylactic acid using said lactic acid as a material (Step D).

6. The method according to claim 5, wherein said Step (D) is a step of direct dehydration polycondensation of lactic acid.

7. A method of producing lactic acid crystal(s) comprising:
   filtering a lactic acid containing aqueous solution through a nanofiltration membrane to recover an aqueous lactic acid solution from the permeate side (Step A);
   distilling said aqueous lactic acid solution to recover lactic acid from the vapor side (Step B), and performing a first stage condensing step to obtain distilled lactic acid from a first condenser vapor side and a second stage condensing step to remove water and a low boiling component(s) from a second condenser vapor side; and
   crystallizing said lactic acid obtained only in the first stage condensing step from Step B, and performing solid-liquid separation to recover a lactic acid crystal(s) (Step C),
   wherein water content of obtained said lactic acid crystal(s) in Step (C) is/are reduced by Steps (A) and (D).

* * * * *